United States Patent [19]

Duffy

[11] 4,026,808

[45] May 31, 1977

[54] FLAME RETARDANT TEXTILE FINISHES

[75] Inventor: James J. Duffy, Buffalo, N.Y.

[73] Assignee: Hooker Chemicals & Plastics Corporation, Niagara Falls, N.Y.

[22] Filed: July 1, 1974

[21] Appl. No.: 485,038

Related U.S. Application Data

[63] Continuation-in-part of Ser. No. 239,785, March 30, 1972, abandoned.

[52] U.S. Cl. .................................. 252/8.1; 428/921
[51] Int. Cl.$^2$ ................. C09D 5/18; C09D 1/00; B27K 3/00
[58] Field of Search ............ 252/8.1; 8/116 P, 184; 428/921

[56] References Cited

UNITED STATES PATENTS

| | | | |
|---|---|---|---|
| 2,832,745 | 4/1958 | Hechenbleikner | 260/29.4 |
| 3,577,270 | 10/1969 | Guth | 117/136 |
| 3,658,791 | 4/1972 | Tesoro | 260/239 EP |
| 3,658,952 | 4/1972 | Nachbur | 260/932 |
| 3,690,941 | 9/1972 | Reuter | 117/136 |
| 3,699,192 | 10/1972 | Moretti | 260/926 |
| 3,700,403 | 10/1972 | Nachbur | 8/115.6 |
| 3,772,068 | 11/1973 | Hofmann | 252/8.1 |
| 3,796,596 | 3/1974 | Daigle | 252/8.1 |
| 3,864,076 | 2/1975 | Nachbur | 252/8.1 |
| 3,884,628 | 5/1975 | Duffy | 252/8.1 |

FOREIGN PATENTS OR APPLICATIONS 1,139,380   1/1969   United Kingdom

OTHER PUBLICATIONS

Aenishanslin, Textile Research Journal, Apr. 1969, pp. 375–381.

*Primary Examiner*—Samuel W. Engle
*Assistant Examiner*—Donald P. Walsh
*Attorney, Agent, or Firm*—Peter F. Casella; William J. Crossetta, Jr.

[57] ABSTRACT

Normally flammable textile materials are rendered flame retardant by the intimate association therewith of a flame retarding amount of a composition comprising a phosphorus containing N-hydroxy-methyl amide and tetrakis(hydroxymethyl) phosphonium chloride.

12 Claims, No Drawings

FLAME RETARDANT TEXTILE FINISHES

FIELD OF INVENTION

This invention relates to a process for rendering flame retardant, normally flammable, textiles such as cellulosic materials, proteinaceous materials and analogous man-made materials by the intimate association therewith of a flame retarding amount of a composition comprising a phosphorus containing N-hydroxymethyl amide and tetrakis(hydroxymethyl) phosphonium chloride.

BACKGROUND OF THE INVENTION

Many flame retarding agents and methods of application have been developed in attempts to obtain flame resistant textile materials.

Flame retardent textiles have been produced by depositing metal oxides, within or on the textile fibers, by the successive precipitation of ferric oxides and a mixture of tungstic acid and stannic oxide or by successive deposition of antimony trioxide and stannic oxide or by successive deposition of antimony trioxide and titanium dioxide. Such processes require plural treatment baths in which strongly acidic solutions are employed thus posing the problem of possible textile degradation. Furthermore, metal oxide coatings on textile materials create difficulties in subsequent dyeing processes which deleteriously affect the hand of the finished product. Another process, involves the use of a single processing bath wherein a dispersion of a chlorinated hydrocarbon and finely divided antimony oxide is padded on the textile material. Near the textile combustion temperature, antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen orthophosphate. Textile products so treated however are subjected to metathesis reaction with cations during washing, and must be regenerated by reacting the wash product with an ammonium chloride solution.

OBJECTS OF THE INVENTION

It is, therefore, a principal object of this invention to provide flame retardant textile materials comprising normally flammable cellulosic, proteinaceous or analogous man-made materials.

Another object is to provide a process for treating normally flammable cellulosic, proteinaceous or analogous man-made materials to render them flame retardant.

A particular object is to devise a composition comprising normally flammable cellulosic, proteinaceous or analogous man-made material and an effective flame retarding amount of a composition comprising a phosphorous containing N-hydroxymethyl amide and tetrakis(hydroxymethyl) phosphonium chloride.

A further object is to provide a process for rendering normally flammable cellulosic, proteinaceous or analogous man-made materials flame retardant by the intimate association therewith of a composition comprising a phosphorus containing N-hydroxymethylamide and tetrakis(hydroxymethyl) phosphonium chloride.

DESCRIPTION OF THE INVENTION

In accordance with this invention, a process is provided for imparting flame retardancy to textile materials by incorporating into or on the textile material a flame retardant amount of a composition comprising one or more phosphorus containing N-hydroxymethyl amides and tetrakis(hydroxymethyl) phosphonium chloride. Phosphorus containing N-hydroxymethyl amides useful in this invention include compounds of the formula.

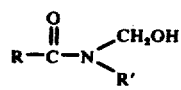

wherein R is independently selected from substituted and unsubstituted amino and hydrocarbon substituents, R' is independently selected from hydrogen and substituted and unsubstituted hydrocarbon substituents, provided at least one of R and R' has a phosphorus substituent thereon. Phosphorus containing N-hydroxymethyl amides encompassed by this invention include:

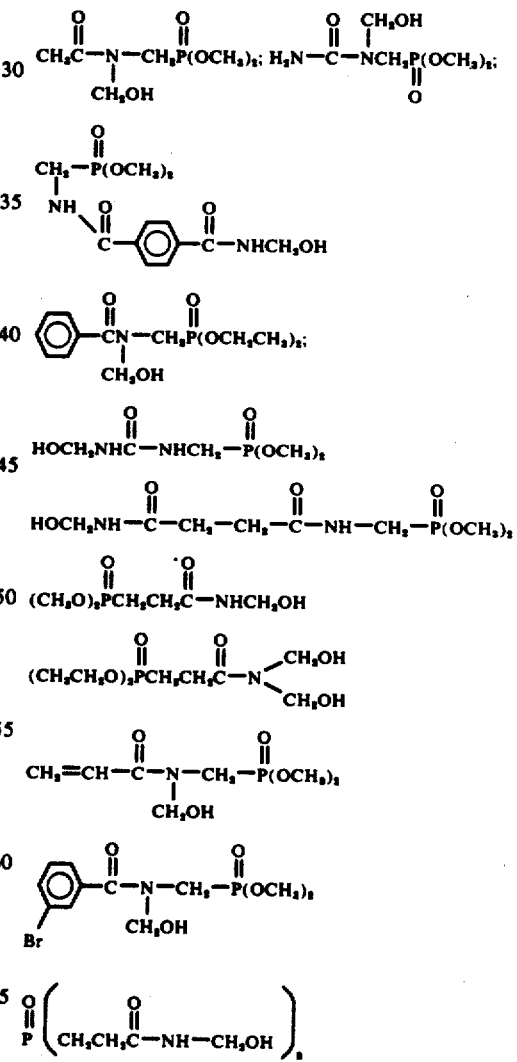

The synthesis of the phosphorus containing N-hydroxymethyl amides of the instant invention may be accomplished by reacting a phosphorus containing amide with formaldehyde in a suitable solvent using standard chemical means. The phosphorus containing amides used in this invention are prepared by standard chemical reactions.

In the practice of this invention the tetrakis(hydroxymethyl) phosphonium chloride (THPC) and phosphorus containing N-hydroxymethyl amides, may be applied to the textile materials by conventional textile finishing techniques, such as by thermal induced pad curing, so to incorporate into the textile a flame retardant amount thereof. The compounds of this invention have advantages over the flame retardant agents of the prior art in that they may be used on a variety of textile materials of different chemical compositions, and they may be applied by a variety of methods. They may be applied to materials either in the fiber or fabric form to give flame retarding materials with minimum detectable physical changes in the quality or hand of the textile material.

Generally only small amounts of THPC need be present in the composition, in relation to the amount of phosphorus containing N-hydroxymethyl amide, to greatly affect the efficiency of the latter as a flame retardant. Typically, mole ratios of THPC of phosphorus containing N-hydroxymethyl amide from about 1:1 to about 0.05:1 and preferably from about 0.20:1 to about 0.10:1 act to increase the resin add-on of the phosphorus containing N-hydroxymethyl amide which results in a greatly increased flame retarding efficiency thereof and increased durability to laundering. The amount of flame retardant composition utilized in the process of this invention, depends upon the type, weave and weight of the textile and is measured by weight of flame retardant added thereto. Generally from about 5 to about 50% by weight of textile, of the flame retardant composition is added to the textile, from about 10 to about 30% being preferred.

Cellulosic textile materials may be made flame retardant by way of a variety of methods. Typically, the cellulose is immersed in an aqueous solution of the flame retardant composition of this invention. (20 to 70% by weight) and squeezed, using a two role padder at about 60 lbs. per square inch gauge pressure, to from about 60 to about 120% wet weight pick-up, based upon the weight of textile. The materials are then dried in a circulating air oven at about 150° to about 450° Fahrenheit or preferably from about 200° to about 275° Fahrenheit for about 1 to about 10 minutes to promote drying. The materials are then cured in a circulating air oven at about 250° to 450° F or preferably from about 300° to 370° F for about 1 to 10 minutes to promote reaction. Drying and curing may be completed in one step but a separate dry and cure is preferable. Thereafter the samples are washed in hot water to remove residual unreacted material and dried.

The flame retardant agents of this invention may be applied to various textiles such as cellulosic materials, proteinaceous materials and blends of cellulosic or proteinaceous materials with polyethylene terephthalate and analogous man made fibers. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs. Of special interest is the applicability of fire retardant agents of the instant invention to analogous man made fibers such as blends of cotton polyethylene terephthalate, in textile fabrics and fibers to provide a uniform, flame retardant finish.

It should be noted that it is within the scope of the present invention to incorporate such ingredients as plasticizers, dyes, pigments, stabilizers, antioxidants, antistatic agents and the like to the novel flame retardant composition.

In each of the examples the process steps were performed as follows except where a specific method is otherwise indicated. Padding was accomplished by dipping the sample in the requisite solution for about a second and immediately thereafter nipping the thus treated sample on a two role laboratory padder at about 60 pounds per square inch gauge pressure to a wet pickup of about 90%. Scouring was accomplished by subjecting the sample to one complete cycle of washing, rinsing and spin drying in a standard, automatic, home-type washing machine utilizing 40 grams of "Tide" detergent. Tumble drying was done in a standard, home-type, automatic, circulating-air, tumble dryer. Flammability testing was done in accordance with the American Association of Textile Chemists and Colorists (AATCC) test method 34-1969, the standard vertical char method. Therein, 2¾ × 10 in. test specimens are exposed to a controlled burner flame under controlled conditions for a period of 3.0 seconds. The chared specimens are thereafter subjected to controlled tearing tests, using tabulated weights, and the average tear length is measured as representing the char length of the flame retardant treated fabric. In each of the examples, the indication of a char distance for the sample indicates self-extinguishment at that point. For comparison purposes the corresponding non-treated textile sample would be consumed. A Hooker Boil (HB) is done in a standard, center post, wringer washer fitted with internal steam coils. The sample to be treated is washed and agitated therein for 45 minutes in a solution containing 88 pounds of water, 100 grams of sodium carbonate, 100 grams of "Ivory" soap and 10 grams of Tide detergent at a temperature of about 200° to about 210° Fahrenheit. The washer is then drained, the sample squeezed through the wringer and again washed and agitated therein for 15 minutes in about 88 pounds of water at about 140° to about 160° Fahrenheit.

The following examples are set forth for purposes of illustration only and are not to be construed as limitation to the present invention except as set forth in the appended claims. Resin 23 special used therein is a type of commercially available methylolated melamine containing 50% solids in aqueous solution. Tetrakis(hydroxymethyl) phosphonium chloride (THPC) used therein is 100% solids.

All parts and percentages are by weight unless otherwise specified.

EXAMPLE I

A sample of 5.0 ounce per square yard of cotton sheeting, was padded with a solution containing 100 parts of Resin 23 special, 50 parts of 40% aqueous formalin solution, 20 parts of $Zn(NO_3)_2 \cdot 6H_2O$ and 150 parts of water to a wet pick-up of about 90% by weight of sample. The thus treated sample was then dried at about 250° F for 2 minutes and cured at about 320° F for 5 minutes in a circulating air oven. The sample was then scoured for one complete wash cycle in a home type washer and thereafter tumble dried. The treated sample when tested by AATCC method 34-1969, was consumed. In a similar manner when samples of wool and 35% cotton polyethylene terephthalate are treated by the same method and tested by AATCC method 34-1969, the samples are consumed.

EXAMPLE II

A sample of 5.0 ounce per square yard of cotton sheeting is treated, in accordance with Example I, with a solution containing 100 parts of Resin 23 special, 50 parts of 40% aqueous formalin solution, 20 parts of $Zn(NO_3)_2.6H_2O$, 150 parts of water and 25 parts of THPC. Upon subjecting the sample to AATCC test method 34-1969, it is consumed. In a similar manner when samples of wool and 35% cotton polyethylene terephthalate are treated by the same method and tested by AATCC method 34-1969, the samples are consumed.

EXAMPLE III

A sample of 5.0 ounce per square yard of cotton sheeting was padded with a solution containing 200 parts of

100 parts of Resin 23 Special, 50 parts of 40% aqueous formalin solution, 20 parts of $Zn(NO_3)_2.6H_2O$ and 150 parts of water to a wet pickup of about 90% by weight of sample and thereafter treated in the manner of Example I. The treated sample was found to have a resin add-on of about 11.3% and, when tested by AATCC method 34-1969 had a calculated char length of 5.9 inches. The sample was then subjected to one Hooker Boil and, after tumble drying, when tested by AATCC Method 34-1969 was consumed.

EXAMPLE IV

A sample of 5.0 ounce per square yard of cotton sheeting was padded with a solution containing 200 parts of

100 parts of Resin 23 Special, 50 parts of 40% aqueous formalin solution, 20 parts of $Zn(NO_3)_2.6H_2O$, 150 parts of water and 25 parts of THPC to a wet pickup of about 90% by weight of sample and thereafter treated in the manner of Example II. The treated sample was found to have a resin add-on of about 15.1% and when initially tested by AATCC method 34-1969 had a calculated char length of 3.9 inches. After one Hooker Boil and tumble drying the AATCC method 34-1969 tested sample had a calculated char length of 5.7 inches. After two more Hooker Boils and tumble drying the AATCC method 34-1969 tested sample had a calculated char length of 7.9 inches.

EXAMPLE V

A sample of 5.0 ounce per square yard of cotton sheeting was padded with a solution containing 200 parts of 80%

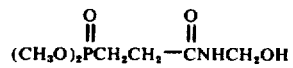

commercially known as Pyrovatex CP, 100 parts of Resin 23 special, 20 parts of $Zn(NO_3)_2.6H_2O$ and 200 parts of water to a wet pickup of about 90% by weight of sample and thereafter treated in the manner of Example III. The treated sample was found to have a resin add-on of about 16.1% and then initially tested by AATCC method 34-1969 had a calculated char length of 5.9 inches. After one Hooker Boil and tumble drying the AATC method 34-1969 tested sample had a calculated char length of 6.0 inches. After two or more Hooker boils and tumble drying the sample was consumed when tested by AATCC method 34-1969.

EXAMPLE VI

A sample of 5.0 ounce per square yard of cotton sheeting was treated in the same manner of Example IV with the exception that the solution additionally contained 25 parts of THPC in replacement of 25 parts of water. Resin add-on was about 27.3% initial char 5.1 inches, char after one HB was 5.0 inches and after two additional HB's 4.1 inches.

EXAMPLE VII

A sample of 6.0 oz. per square yard wool was padded with a solution containing 20 parts of

20 parts of resin 23 Special, 20 parts of aqueous 40% formalin solution, 5 parts of zinc nitrate hexahydrate, 1 part of a non ionic wetting agent and 49 parts of water to a wet pickup of 98% by weight of sample. The thus treated sample was then dried at about 240° F for about 2.5 minutes and cured at about 340° F for about 5 minutes in a circulating air oven. The sample was then washed by hand in a water detergent mixture for about 5 minutes and pressed dry. The treated sample was found to have a resin add-on of about 5.2% and, when tested by AATCC method 34-1969 had a calculated char length of 7.8 inches. The sample was then subjected to 5 washes in a standard home type automatic washer with Tide detergent, and tumble dried. When tested by AATCC Method 34-1969 the thus treated sample was consumed.

EXAMPLE VIII

A sample of 6.0 ounce per square yard wool was treated in the same manner as Example VII with the exception that the solution additionally contained 5 parts of THPC. Resin add-on was 7.9% and initial char length 3.8 inches. After 5 washings and dryings, the char length tested as 5.8 inches and after 15 additional washings and dryings was 5.9 inches.

EXAMPLE IX

A sample of polyester/cotton (35/65) flannel of 4.1 oz. per square yard was padded through a solution containing 40 parts of

20 parts of Resin 23 Special, 6 parts of zinc nitrate hexahydrate, 1 part of a nonionic wetting agent and 49 parts of water to a wet pickup of 73% by weight of sample. The thus-treated sample was then dried at about 240° F for about 2 minutes and cured at about 330° F for about 6 minutes in a circulating air oven. The sample was then washed, with Tide detergent, for one complete wash cycle in a standard home type automatic washer and tumble dried. The treated sample was found to have a resin add-on of 13.4% and when tested by AATCC Method 34-1969 had a calculated char length of 7.3 inches. The sample was then subjected to one Hooker Boil and tumble dried. When tested by AATCC Method 34-1969 the sample was consumed.

EXAMPLE X

A sample of 4.1 oz/square yard cotton flannel of 35/65 polyester cotton composition was treated in the same manner as Example IX with the exception that the solution additionally contained 10 parts of THPC. Resin add-on was 23.1% and initial char was 5.2 inches. After subjection to one Hooker boil the char length tested as 4.9 inches, and after 3 Hooker boils, 6.3 inches.

I claim:

1. A flame retarding composition comprising tetrakis (hydroxymethyl) phosphonium chloride and a phosphorus containing N-hydroxymethyl amide in a mole ratio from about 1:1 to about 0.05:1, of the formula $$R-\overset{O}{\underset{\|}{C}}-N\overset{CH_2OH}{\underset{R'}{\diagdown}}$$

wherein R is independently selected from substituted and unsubstituted amino and hydrocarbon substituents; R' is independently selected from hydrogen and substituted and unsubstituted hydrocarbon substituents, providing at least one of R and R' has a phosphorus substituent thereon.

2. The composition of claim 1 wherein said N-hydroxymethyl amide is

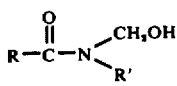

3. The composition of claim 1 wherein said N-hydroxymethyl amide is

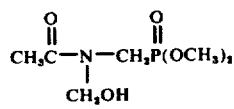

4. The composition of claim 1 wherein said N-hydroxymethyl amide is

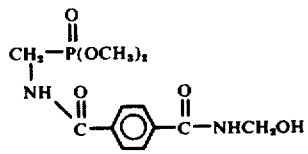

5. The composition of claim 1 wherein said N-hydroxymethyl amide is

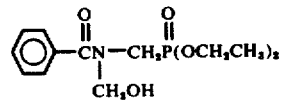

6. The composition of claim 1 wherein said N-hydroxymethyl amide is

7. The composition of claim 1 wherein said N-hydroxymethyl amide is $$HOCH_2NH-\overset{O}{\underset{\|}{C}}-CH_2-CH_2-\overset{O}{\underset{\|}{C}}-NH-CH_2-\overset{O}{\underset{\|}{P}}(OCH_3)_2$$

8. The composition of claim 1 wherein said N-hydroxymethyl amide is $$(CH_3O)_2PCH_2CH_2C-NH-CH_2OH$$

9. The composition of claim 1 wherein said N-hydroxymethyl amide is

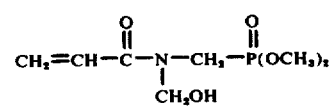

10. The composition of claim 1 wherein said N-hydroxymethyl amide is

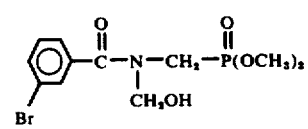

11. The composition of claim 1 wherein said N-hydroxymethyl amide is

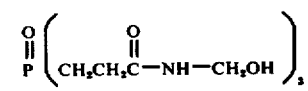

12. The composition of claim 1 wherein said N-hydroxymethyl amide is

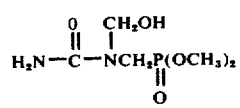

* * * * *